(12) United States Patent
Alley et al.

(10) Patent No.: US 7,631,657 B2
(45) Date of Patent: Dec. 15, 2009

(54) EXPLUSION VALVE ASSEMBLY

(75) Inventors: Randall Alley, Thousand Oaks, CA (US); Adam Soss, Winnetka, CA (US); Dustin Bouch, Petaluma, CA (US)

(73) Assignee: Otto Bock Healthcare GmbH, Duderstadt (DE)

(*) Notice: Subject to any disclaimer, the term of this patent is extended or adjusted under 35 U.S.C. 154(b) by 310 days.

(21) Appl. No.: 11/287,647

(22) Filed: Nov. 28, 2005

(65) Prior Publication Data
US 2006/0289070 A1    Dec. 28, 2006

Related U.S. Application Data

(63) Continuation-in-part of application No. 11/168,956, filed on Jun. 28, 2005, now Pat. No. 7,448,407.

(51) Int. Cl.
*F16K 15/00* (2006.01)

(52) U.S. Cl. .................. 137/543; 137/540; 285/317; 285/320; 623/33

(58) Field of Classification Search .............. 137/269, 137/540, 542, 543; 285/317, 320, 321; 623/33–37
See application file for complete search history.

(56) References Cited

U.S. PATENT DOCUMENTS

| | | | | |
|---|---|---|---|---|
| 5,658,353 A | * | 8/1997 | Layton | 623/34 |
| 5,895,429 A | * | 4/1999 | Cool et al. | 623/35 |

* cited by examiner

*Primary Examiner*—Kevin L Lee
(74) *Attorney, Agent, or Firm*—Faegre & Benson, LLP (57) ABSTRACT

A valve assembly having a threadless base and a removable threadless insert that separately contains a check valve piece. The check valve piece is resiliently supported to abut a seal fitted to the insert. In one assembly, a pair of resiliently biased latch arms restrain the insert to the base. Flanges at the latch arms are resiliently biased to flex and grip the base as the insert is pushed into the base. Insert removal is effected with the release and lifting of the latch arms. In another assembly, the insert is magnetically coupled to the base and a resiliently biased check valve piece and setscrew adjuster regulates flow pressure.

25 Claims, 7 Drawing Sheets

EXPLUSION VALVE ASSEMBLY

RELATED APPLICATION INFORMATION

This is a continuation-in-part of application Ser. No. 11/168,956 filed Jun. 28, 2005, now U.S. Pat. No. 7,448,407.

FIELD OF THE INVENTION

The present invention relates to check valves and in particular to latched and magnetic valve assemblies used to maintain a preferred suspension pressure at a prosthetic socket or interface between a limb and a prosthesis, among other applications.

BACKGROUND OF THE INVENTION

The maintenance of a negative pressure or suction in a prosthetic socket or at a related interface to thereby facilitate a desired limb suspension is typically achieved through the use of an expulsion-type check valve (e.g. auto, manual or both). Such valves are typically configured to provide a threaded base or seat. The base, in turn, normally supports a threaded valve insert that is configured to ensure a proper airtight seal.

Proper placement of the valve insert relative to the base requires a high degree of dexterity and hand-eye coordination, especially when used in a prosthetic limb. That is, most typically the valve base is located at the most distal aspect of a limb socket. The base is typically thermoformed or laminated into the socket. Such a location can be difficult to see, but can also present an awkward relative alignment angle to mount or detach the valve insert.

Because the valve threads, which exhibit a relatively fine pitch, have to line up perfectly in order for the valve insert to be set properly, the combination of poor visibility and high demands for physical dexterity typically result in difficult donning situations for individuals with sound hands and fingers. Removal of the valve can present similar challenges, as the quality of the seal is often related to how tight the insert has been screwed into the valve base. A significant amount of friction can result from overzealous tightening of the valve insert, making it extremely difficult to remove.

For individuals with an involved upper extremity or extremities (e.g. injured, deformed, diseased or the result of insufficient congenital development), the insertion and/or removal of the valve insert from the valve seat can prove impossible. This circumstance is particularly onerous for the debilitated user who has to periodically self-adjust the limb.

The foregoing difficulties have been overcome with the present valve assembly, which in one construction provides a threadless base that is adapted to receive a mating, latched insert. The valve assembly at the coupling junction between the base and insert is particularly constructed to provide for a latched connection. The interconnection provides a sliding, sealed valve insert piece that is respectively pushed or pulled from the seat or base during mounting and removal. The connection is maintained or broken with cooperating latch arms that assure proper insert retention.

In another construction, a threadless base supports an insert via O'rings and a magnetic coupling. A spring biased valve piece or stem piece having adjustable air pressure release capabilities is concentrically supported in the insert.

SUMMARY OF THE INVENTION

It is a primary object of the present invention to provide a threadless valve assembly wherein a valve base or seat supports a mating, latched insert that contains a valve or stem piece.

It is a further object of the invention to provide a valve assembly having a threadless base.

It is a further object of the invention to provide a valve assembly having a base containing a bore that accepts a slide mounted insert.

It is a further object of the invention to provide a latched interconnection between the valve seat and the insert.

It is a further object of the invention to provide a valve assembly that accepts an insert having pivoting latch arms.

It is a further object of the invention to provide a magnetic coupling between the valve seat and the insert.

It is a further object of the invention to provide a valve assembly wherein O'ring(s) seal a valve insert within a seat bore.

It is a further object of the invention to provide a resiliently biased check valve piece within the valve insert.

It is a further object of the invention to provide a pressure adjustable check valve piece within the valve insert.

The foregoing objects are achieved in a presently preferred valve assembly, which includes a threadless base or seat and a threadless valve insert. The threadless insert is pushed into the base by hand or by using a tool or other appliance that imparts sufficient pressure on the valve insert to overcome an internal resilient tension and seal friction.

The valve seat and valve insert include overlapping, annular flange surfaces. An O'ring seals the insert within the seat. A concentric, resiliently biased stem or check valve piece is retained in the insert with a second O'ring. Resiliently biased latch arms are mounted to the insert and located to pivot during insert insertion and extraction. Flanged latch surfaces at the arms flex outward during insertion and spring back to a concentric, restraining alignment with the base upon traversing an interconnecting annular flange at the base.

During insert removal, portions of the latch arms are depressed and pivoted to disconnect the arms from the base. The insert can then be removed, which action is facilitated if the insert is independently biased with other resilient devices (e.g. springs) fitted between the insert and base. Although two latch arms are symmetrically arranged to the present base, a single latch arm or other arrangements of arms can be used.

A plunger-type stem or check valve piece is used to allow auto or manual expulsion of air or other gas or liquid from the limb socket, although other types and mountings of the stem piece can also be adapted to the insert. Similarly, the stem piece might be latched to the insert in a related manner with latch arms or other threadless restraints. Although the present valve assembly finds particular application with prosthetic limbs, it is to be appreciated the valve might be used in other applications.

In another construction, the valve insert is magnetically coupled to the base. A pair of O'rings facilitate retention and provide a seal action. An adjustable, resiliently biased stem or check valve piece is supported to the insert with an O'ring seal. A set screw cooperates with the insert and a spring to provide a pressure adjustable one-way check valve action.

Still other objects, advantages and constructions of the present invention, among various considered improvements and modifications, will become apparent from the detailed description provided hereinafter. It should be understood that the detailed description and specific examples, while indicating a presently preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein similar reference callouts are used at the various figures, and wherein.

DETAILED DESCRIPTION OF THE PREFERRED EMBODIMENTS

The following description of the preferred embodiment is merely exemplary in nature and is in no way intended to limit the invention, its application, or uses. For purposes of clarity, the same reference numbers are used throughout the drawings to identify similar components.

Figure 1:
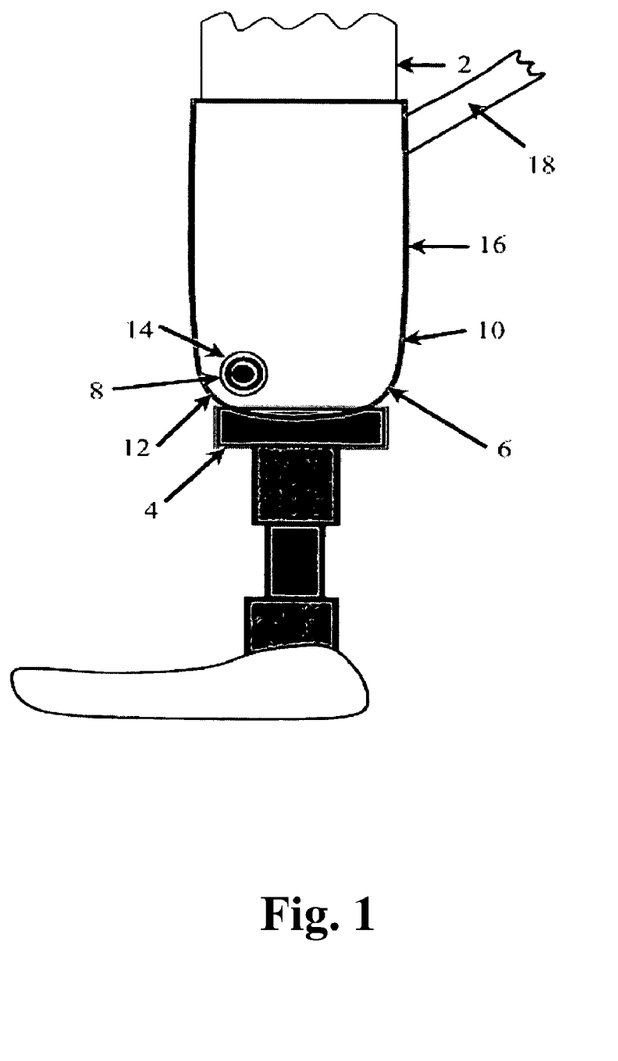
FIG. 1 shows a perspective view to a prosthetic limb that has been adapted to include one construction of a push valve assembly of the invention.

Referring to FIG. 1 a view is shown to a coupling between a limb 2 (e.g. a leg or arm) and a suitable prosthetic appliance 4. A cutaway view is shown to a limb socket 6 at the appliance 4 and where a valve 8 constructed in accord with the subject invention is shown. The valve 8 is fitted to a socket assembly 10 that is used at the interface between the appliance 4 and an extremity of the user's limb 2. The valve 8 is mounted to a socket piece 12 that is shaped to mate with a surgically prepared distal end of the limb extremity. A valve base 14 is typically thermoformed or laminated into the socket piece 12.

A collar or harness 16 is formed to contain the socket piece 12 and shelter the distal end of the extremity. Suitable padding 16 and/or straps 18 are provided at the collar 14 to enhance the durability of the attachment.

Depending upon the limb and application, a principal concern is to maintain a limb to prosthesis connection that provides maximum flexibility without causing limb ulceration. Various interfaces have been developed that use padding materials such as foams, plastics, polyester and acrylic resins etc. Interfaces that incorporate air, gas or liquid buffers or cushions or combinations thereof are also frequently used. It is with respect to prosthetic devices that use gas and/or liquid buffer materials that the valve 8 of the invention finds particular application.

The valve 8 is particularly used at included ports to allow the filling of the socket piece 12 with a suitable gas or liquid interface material between the socket piece 12 and limb extremity. The valve 8 also serves as a check valve to prevent the uncontrolled expulsion of the interface material.

Figure 2:
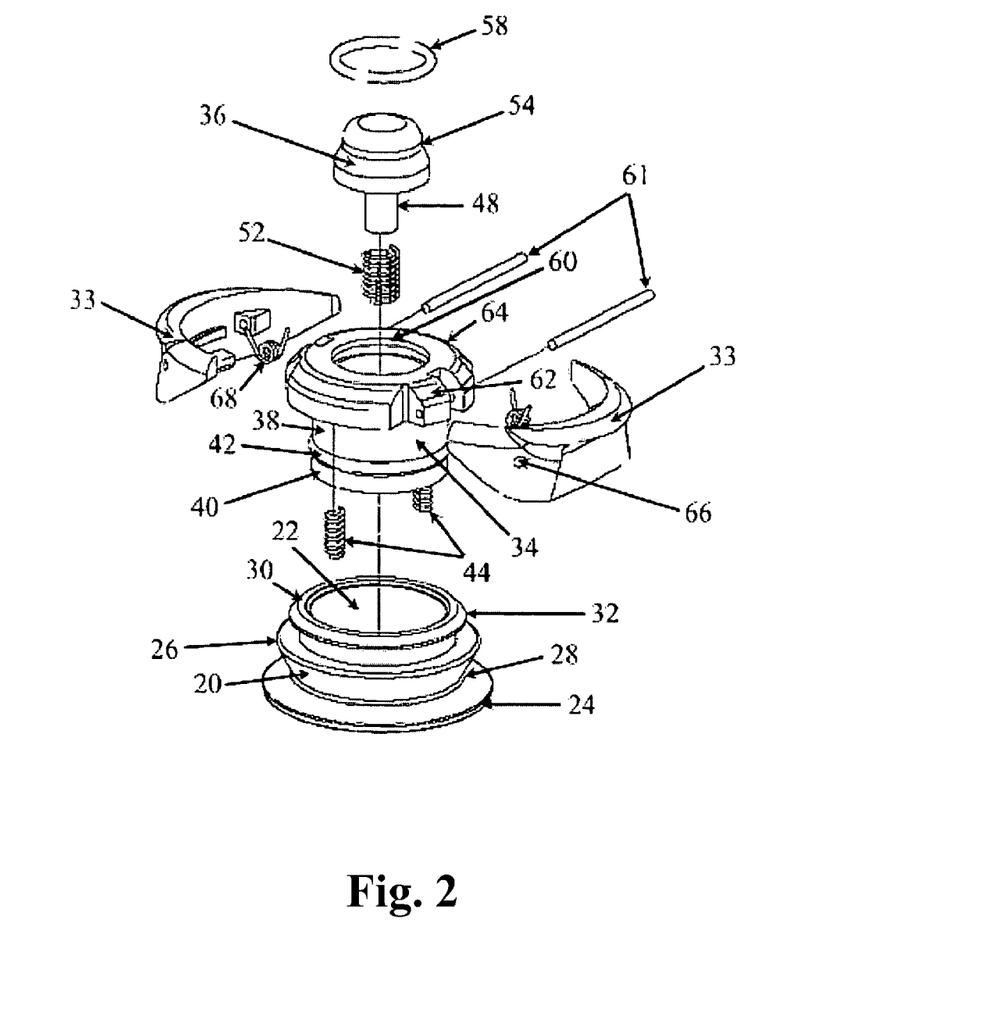
FIG. 2 shows an exploded drawing to the foregoing push valve assembly.

With attention to FIG. 2, the valve 8 is shown in exploded assembly. The valve 8 includes a base 20 that is designed to exhibit a suitable geometric configuration adapted to a preferred mounting of the valve 8. Presently, the base 20 is generally cylindrical in shape, although could exhibit a hexagonal, octagonal or other shape.

A bore 22 longitudinally extends through the base 20. A ringed flange 24 projects from the base 8 and can be laminated to or thermoformed in a socket piece 12 with a variety of suitable adhesives and tapes. The diameter of the flange 24 can be varied as desired.

An adjoining tapered flange surface 26 is also provided that forms a "V", "U" or other suitably shaped groove 28 relative to the flange 24. The groove 28 accommodates valve retention within a thermoformed mounting. Suitable grooves, ridges, knurling or other types of projections and the like can be provided at the surface 26 and groove 28 to facilitate retention to the appliance 4.

A third flanged surface 30 is provided that defines a groove 32 relative to the outermost portion of the flange 26. The groove 32 contains a pair of latch arms 33 that pivot from an associated valve insert 34 to secure the insert 34 and a valve piece 36 at the insert to the bore 22. The details of the mounting of the insert 34 and valve piece 36 are more apparent from the following description with respect to the section views at FIGS. 3, 4 and 5. The flange surfaces 26 and 30 are preferably circularly continuous although can be segmented into a number of discontinuous sections.

The insert 34 provides a generally cylindrical body 38 that is sized to closely mate with the diameter of the bore 22. An annular groove 40 contains an O'ring seal 42. The seal 42 prevents the migration of a gas or liquid contained within the socket piece 12 through the bore 22 and past the insert 34. A pair of springs 44 depend from the body 38 and normally bias the insert 34 to an elevated condition. Although the base 20 and insert 34 are shown in cylindrical shapes, other shapes or combinations of shapes can be adapted as desired. The insert 34 might also be constructed to index to a preferred alignment with the base 20. The springs 44 are supported at their top by recessed holes that receive and maintain the alignment of each spring 44 and are supported at their base by resting on the top edge of the valve base.

A port 46 is aligned to the longitudinal center of the body 38. A stem 48 of the valve piece 36 is separately restrained to the insert 34 at a bore 50 to control liquid or gas flow through the port 46 and bore 50. A spring 52 is supported about the stem 48 in a bore 54 and biases a circular, tapered surface 56 at a head 55 of the valve piece 36 to seal against an O'ring 58 contained at a groove 60 within the bore 54.

The valve piece 36 thus acts as a check valve and prevents flow through the bores 54, 50 and port 46, unless the valve piece 36 is depressed from contact with the O'ring seal 58. It is to be appreciated a variety of other resilient devices and materials can be used to bias the valve piece 36. Similarly, different seat/seal arrangements can be configured between the valve piece 36 and bore 54 to control flow through the bores 46, 50 and 54. The valve piece 36 may also be mounted such that it is normally depressed against the port 46 versus being raised above the port 46, such as with the aid of a snap ring (not shown) and spring 52 mounted to bias the stem 48 to engage the port 46.

The insert 34 is restrained to the base 20 with the latch arms 33 which are mounted to pivot about pivot pins 61. The pins 61 mount through segmented portions 62 of a flange 64 that radiates from the sidewalls of the insert 34 and nest within aligned bores 66 in the arms 33. A torsion spring 68 is fitted around each pin 60 and between the flange 64 and arms 33. The ends of the springs 68 are retained to induce flanges 70 in the arms 33 to pivot inward. Thus, the flanges 70 are restrained beneath the flange 30 in the base 20 and secured to the groove 32, once the insert 34 is fully seated within the base 20. Although two latch arms 33 are presently used, a single arm or additional arms might alternatively be incorporated into the assembly 8. The flanges 70 might also be restrained to depressions or projections.

Figure 3:
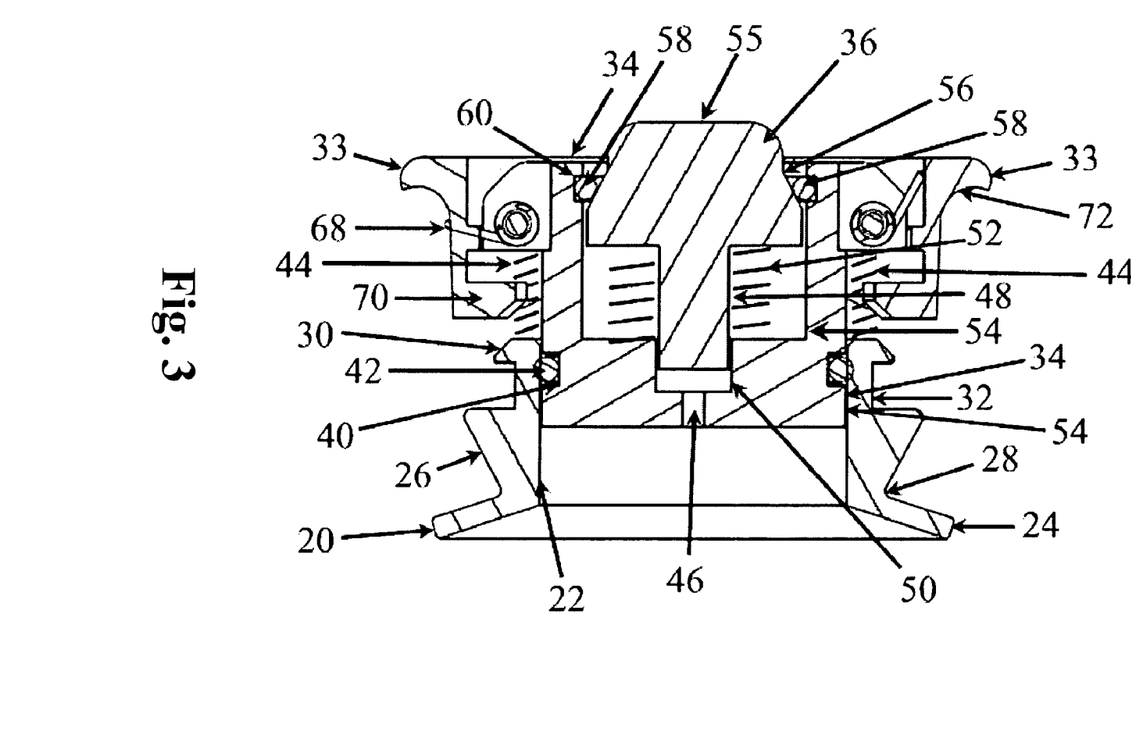
FIG. 3 shows a cross section drawing to the valve assembly at an initial insertion position or just prior to complete removal of the insert from the valve base.
Figure 4:
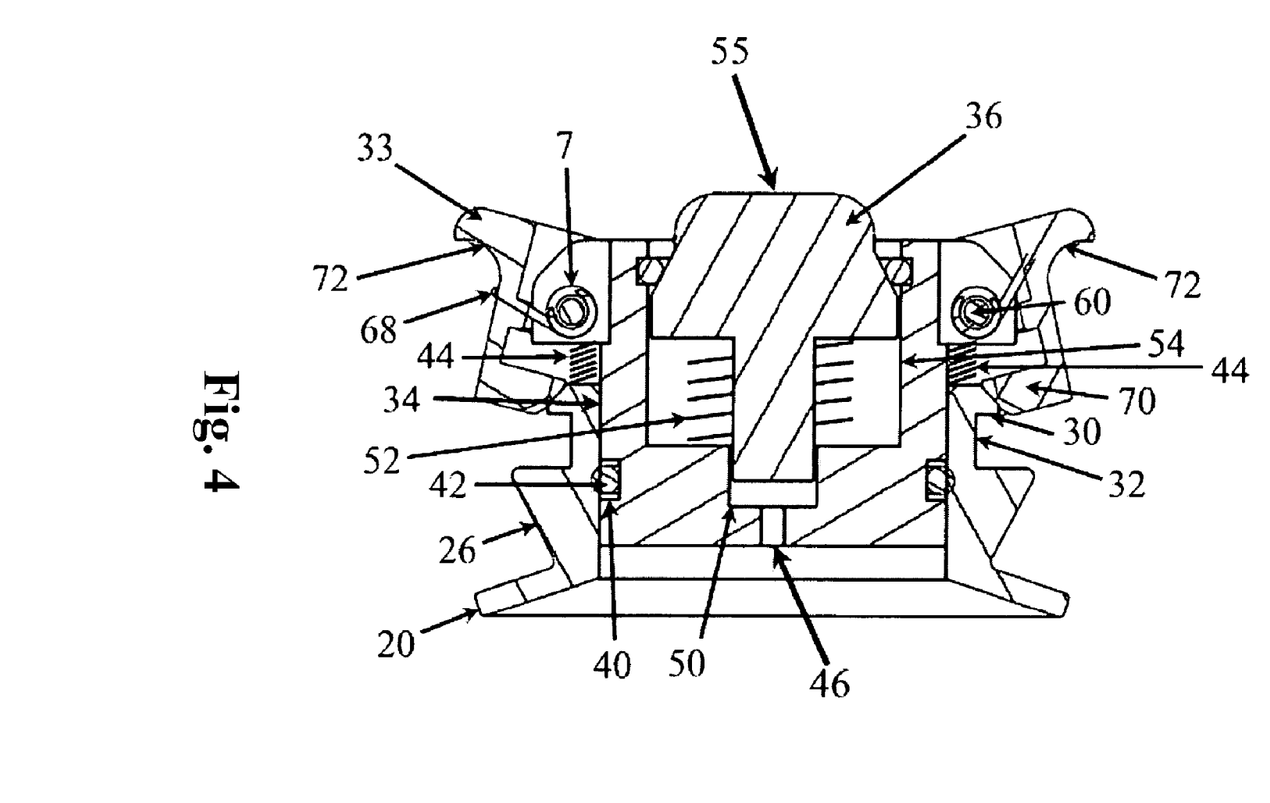
FIG. 4 shows a cross section drawing to the valve assembly with the latch arms squeezed toward one another in preparation for full insertion or removal.
Figure 5:
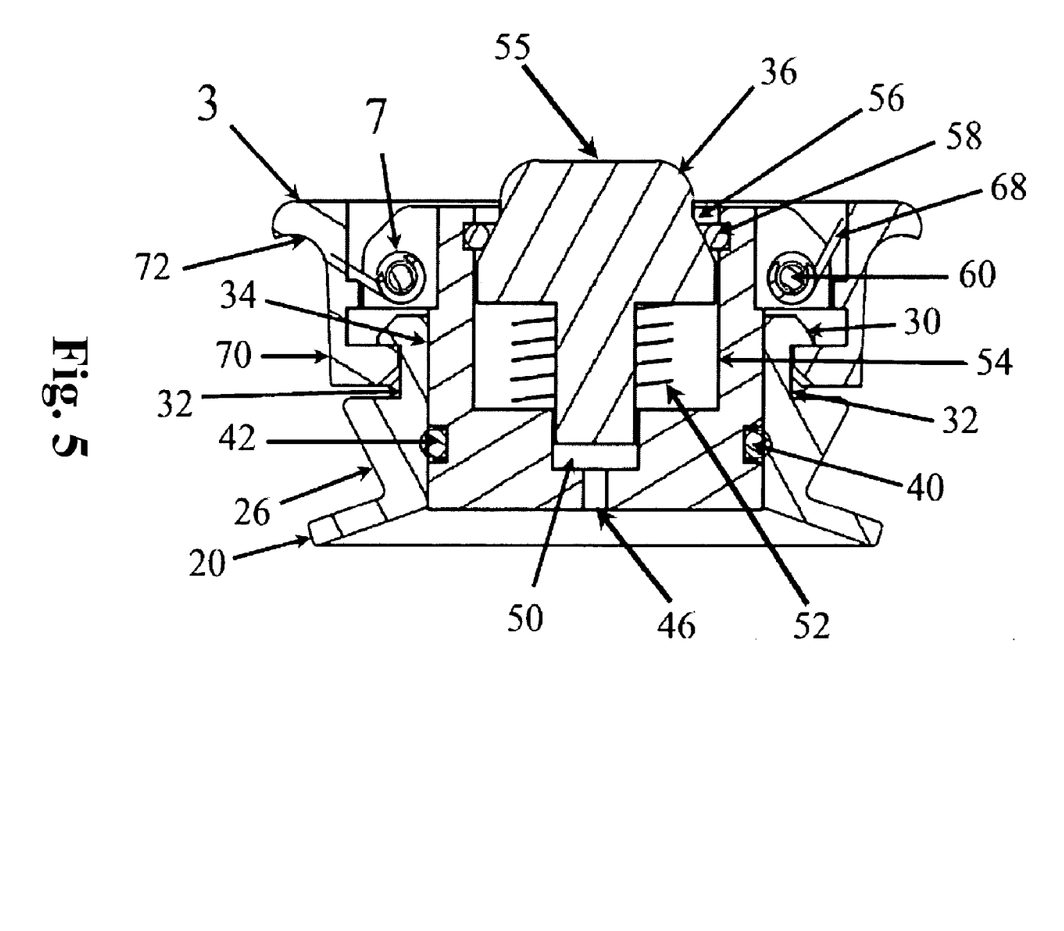
FIG. 5 shows a cross section drawing to the valve assembly with the latch arms latched closed to contain a concentric expulsion valve piece contained within the valve base.

In the latter regard, attention is drawn to FIGS. 3, 4 and 5 and wherein the flanges 70 at the arms 33 are respectively shown in a depressed condition at FIG. 3, a partially flexed condition at FIG. 4 and a seated condition at FIG. 5. During normal mounting, the insert 34 is merely aligned to the base 20 and the tapers at the flanges 70 and 30 induce the flange arms 33 to pivot outward, reference FIGS. 3 and 4. Once the insert 34 is pushed past the flange 30, the flanges 70 spring inward and are captured in the groove 32, reference FIG. 5.

The valve piece 36 mounts merely by suitably lubricating the piece 36 and depressing it and the spring 52 into the bore 54. Removal of the insert 34 is effected by manually lifting up on the finger depressions 72. A typical user of a prosthesis 4 having an air or liquid interface material is thereby now able to readily fit and make suitable adjustments to enhance the fit and comfort of the prosthesis.

Figure 6:
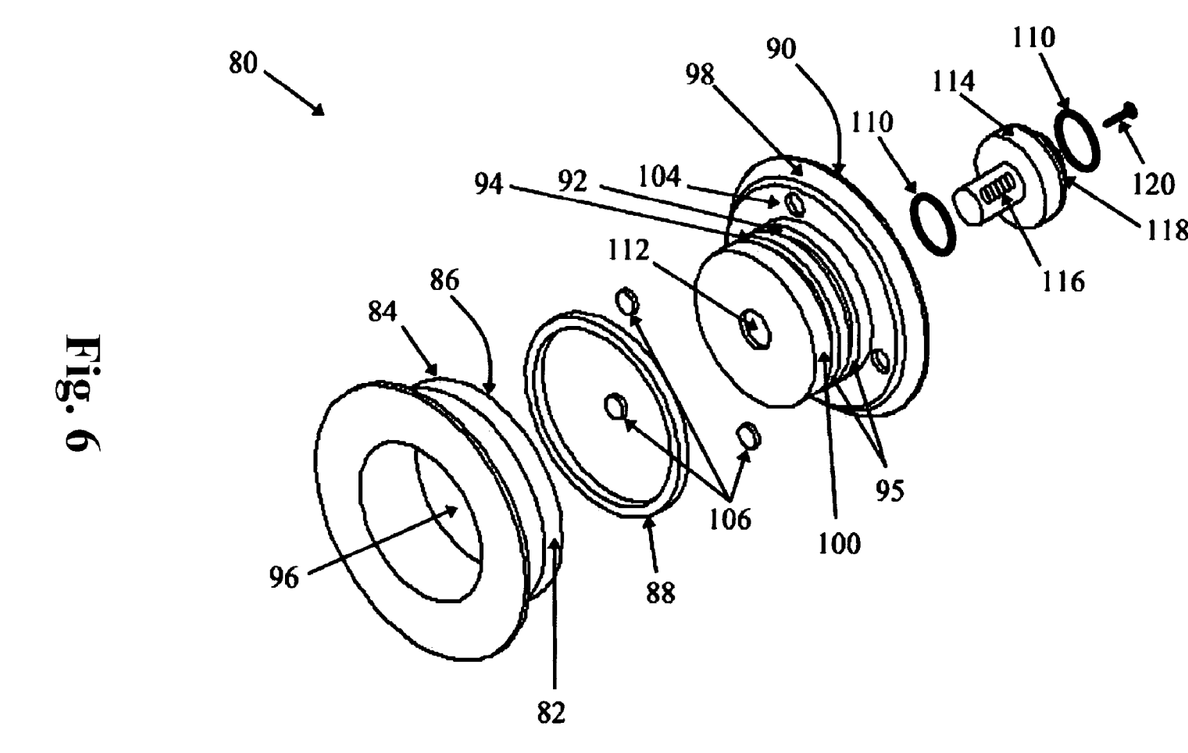
FIG. 6 shows an exploded assembly drawing in perspective view to a magnetic valve assembly containing a concentric expulsion valve within a threadless valve base.
Figure 7:
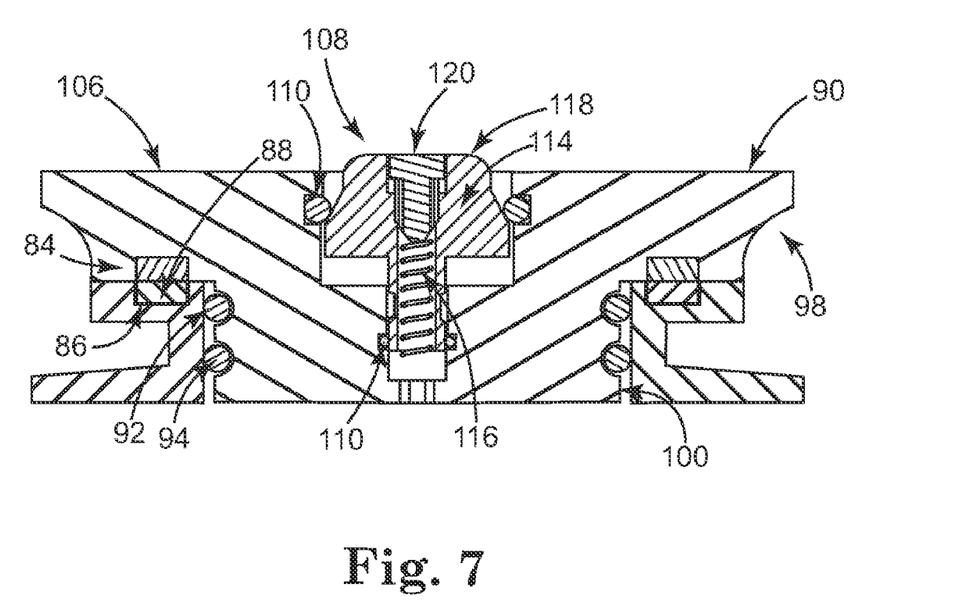
FIG. 7 shows a cross section drawing to the valve assembly of FIG. 6.

Appreciating the efficacy of the improved valve assembly 8 and with attention to FIGS. 6 and 7, another threadless valve assembly 80 is shown in exploded assembly and cross-section, respectively. The assembly 80 includes a seat or base 82 constructed of a suitable thermoplastic, resin or other biocompatible material that can be molded or laminated into place in a socket assembly 10. The seat 82 is similar to the seat 20 except lacks a flange 30 and groove 32. Instead, a raised surface 84 includes a groove 86 that supports a ferromagnetic ring 88 or other suitable magnetically compatible structure that couples to a valve insert 90.

The ring 88 can be constructed of a variety of magnetically compatible materials. Alternatively and among some of other variations, the seat 82 can be constructed of a magnetically compatible material, the surface 84 can include segmented ferromagnetic sections or can be impregnated with iron or similar particles.

The valve insert 90 mounts within the seat 82 and supports upper and lower O'rings 92 and 94 that cooperate with a bore 96. A flange 98 radiates outward from a stem 100 that contains the O'rings 92 and 94 in grooves 95. The O-rings 92 and 94 prevent the passage of air or other buffer material between the insert 90 and seat 82.

Displaced around a surface 104 of the flange 98 are a number of magnets 106 that are mounted to optimally interact with the ring 88 or other magnetic structure at the seat 82. Alternatively and as with the ring 88, the flange 98 can be constructed of a ferromagnetic material, can be impregnated with iron or similar particles or can include segmented ferromagnetic sections that are mounted in registry with the magnets 106.

A check valve assembly 108 mounts to the insert 90 and cooperates with an O'ring seal 110 mounted in a bore 112 of the insert 90 to provide for a one-way flow of the buffer material. The assembly 108 includes a plunger/stem or valve piece 114 and a spring 116 that is supported to resiliently interact with the insert 90 and maintain a flanged cap/valve surface 118 in contact with the O-ring 110.

A setscrew 120 extends through the stem 114 and is threaded to the insert 90. The screw 120 can be adjusted to control the tension at the spring 116 and contact tension between the cap 118 and seal 110. The pressure necessary to overcome the seal can thereby be regulated to automatically provide for a preferred one-way flow (e.g. inside to outside) of the buffer material (e.g. air, other gas or liquid).

From the foregoing, it is to be appreciated the described construction of the complete valve assemblies 8 and 80 are merely exemplary of a presently preferred valve. From the suggested modifications and others that may be apparent to those skilled in the art, it also is to be appreciated the invention can be implemented in still other configurations. Still further, selected portions of the valve assemblies might be adapted into other valve assemblies. The scope of the invention should therefore not be construed merely to the foregoing description, but rather should be construed within the broader scope of the following claims.

What is claimed is:

1. A valve comprising:
   a) a base having i) a body and through which a bore extends, and ii) a magnetic portion;
   b) a first seal and a second seal;
   c) an insert having a body adapted to mount in the bore of said base and engage said first seal with said first seal having a portion between said insert and said base, and including a magnetic portion, wherein the insert body includes a flow bore and wherein the magnetic portion of the insert is mounted to interact with the base magnetic portion and couple said insert to said base, whereby said insert can be inserted, restrained and withdrawn from said base upon overcoming the magnetic attraction between the coupled base and insert; and
   d) a valve piece having a stem adapted to mount in the bore of said insert and wherein a surface of said valve piece mates in sealing engagement with the second seal having a portion disposed between said insert at said flow bore and said valve piece.

2. A valve as set forth in claim 1 wherein said insert includes a flange that aligns to a magnetic surface of said base and including a plurality of magnets mounted to said flange and aligned to magnetically couple to the magnetic portion of said base.

3. A valve as set forth in claim 1 wherein said base includes a magnetically permeable ring.

4. A valve as set forth in claim 1 including a resilient member mounted to resiliently bias said valve piece.

5. A valve as set forth in claim 1 wherein an adjustable member mounts to said valve piece to vary a range of movement of said adjustable member.

6. A valve as set forth in claim 5 wherein said adjustable member is a setscrew.

7. A valve as set forth in claim 1 wherein said first and second seals comprise O'rings.

8. A valve as set forth in claim 1 wherein the base body includes an annular groove and a magnetically permeable ring mounted in said groove.

9. A valve as set forth in claim 1 including a spring member mounted to resiliently bias said valve piece and a setscrew mounted to said insert to vary the tension of said spring, whereby a pressure to overcome the seal of said valve piece can be varied.

10. A valve as set forth in claim 1 wherein the magnetic portion of said insert comprises a plurality of magnetic surfaces and wherein the magnetic portion of said base comprises a circularly aligned magnetic surface.

11. A valve as set forth in claim 1 wherein the magnetic portion of said insert comprises a plurality of magnetic surfaces and wherein the magnetic portion of said base comprises a plurality of aligned magnetic surfaces.

12. A valve as set forth in claim 1 wherein the first seal and the second seal are supported by the insert.

13. A valve comprising:
   a) a base having i) a body and through which a bore extends, and ii) a magnetically permeable portion;
   b) a first O'ring seal and a second O'ring seal;
   c) an insert having a body adapted to mount in the bore of said base and engage said first seal with said first O'ring seal having a portion between said insert and said base, and including a magnetic portion, wherein the insert body includes a flow bore, and wherein the magnetic portion of the insert is mounted to interact with the base magnetic portion and couple said insert to said base, whereby said insert can be inserted, restrained and withdrawn from said base upon overcoming the magnetic attraction between the coupled base and insert; and
   d) a valve piece having a stem adapted to mount in the bore of said insert and a resilient member mounted to bias a surface of said valve piece into sealing engagement with the second seal having a portion disposed between said insert at said flow bore and said valve piece.

14. A valve as set forth in claim 13 wherein said insert includes a flange that aligns to a magnetic surface of said base and including a plurality of magnets mounted to said flange and aligned to magnetically couple to the magnetic portion of said base.

15. A valve as set forth in claim 13 wherein the magnetic portion of said base comprises an annular magnetically permeable surface.

16. A valve as set forth in claim 15 wherein the annular magnetically permeable surface comprises a magnetically permeable ring mounted to said base.

17. A valve as set forth in claim 13 including a spring member mounted to resiliently bias said valve piece and a setscrew mounted to said insert to vary the tension of said spring, whereby a pressure to overcome the seal of said valve piece can be varied.

18. A valve as set forth in claim 13 wherein the first O'ring seal and the second O'ring seal are supported by the insert.

19. A valve comprising:
   a) a base having i) a body and through which a bore extends, and ii) an annual magnetically permeable surface;
   b) a first seal and a second seal;
   c) an insert having a body adapted to mount in the bore of said base and engage said first seal with said first seal having a portion between said insert and said base, and including a flange having a plurality of magnets aligned to couple to the magnetically permeable surface of said base, wherein the insert body includes a flow bore, whereby said insert can be inserted, restrained and withdrawn from said base upon overcoming the magnetic attraction between the coupled base and insert: and
   d) a valve piece having a stem adapted to mount in the bore of said insert and a resilient member mounted to bias a surface of said valve piece into sealing engagement with the second seal having a portion disposed between said insert at said flow bore and said valve piece.

20. A valve as set forth in claim 19 including a spring member mounted to resiliently bias said valve piece and a setscrew mounted to said insert to vary the tension of said spring, whereby a pressure to overcome the seal of said valve piece can be varied.

21. A valve as set forth in claim 19 wherein the annular magnetically permeable surface comprises a magnetically permeable ring mounted to said base.

22. A valve as set forth in claim 19 wherein the first seal and the second seal are supported by the insert.

23. A valve as set forth in claim 19 wherein the first seal and the second seal each comprise O'rings.

24. An expulsion valve for a prosthetic device, the valve comprising:
   a) a valve base defining an air passage and a receptacle portion, the air passage communicating with the receptacle portion;
   b) a threadless valve insert for fitting within the receptacle for sealing the air passage when held in a seated position; and
   c) a first member attached to said base and a second member attached to said valve insert, the first and second members having a magnetic attraction when said valve insert is seated in said receptacle to hold said valve insert in the seated position.

25. The expulsion valve of claim 24, wherein the first member comprises a ferromagnetic ring and the second member comprises magnets.

* * * * *

UNITED STATES PATENT AND TRADEMARK OFFICE
CERTIFICATE OF CORRECTION

PATENT NO. : 7,631,657 B2　　　　　　　　　　　　　　　　　　　　　　　Page 1 of 1
APPLICATION NO. : 11/287647
DATED : December 15, 2009
INVENTOR(S) : Alley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 491 days.

Signed and Sealed this

Second Day of November, 2010

David J. Kappos
*Director of the United States Patent and Trademark Office*